US 8,409,199 B2

(12) United States Patent
Herzon

(10) Patent No.: US 8,409,199 B2
(45) Date of Patent: Apr. 2, 2013

(54) THERMAL CAUTERY SURGICAL FORCEPS

(76) Inventor: Garrett D. Herzon, Los Angeles, CA (US)

( * ) Notice: Subject to any disclaimer, the term of this patent is extended or adjusted under 35 U.S.C. 154(b) by 0 days.

(21) Appl. No.: 13/339,408

(22) Filed: Dec. 29, 2011

(65) Prior Publication Data

US 2012/0101486 A1     Apr. 26, 2012

Related U.S. Application Data

(60) Division of application No. 12/577,531, filed on Oct. 12, 2009, now Pat. No. 8,128,623, which is a continuation of application No. 11/512,159, filed on Aug. 30, 2006, now abandoned, which is a continuation of application No. 10/326,387, filed on Dec. 23, 2002, now abandoned, which is a continuation of application No. 09/842,140, filed on Apr. 26, 2001, now Pat. No. 6,533,778, which is a continuation of application No. 09/235,229, filed on Jan. 21, 1999, now Pat. No. 6,235,027.

(51) Int. Cl.
   *A61B 18/04*     (2006.01)
(52) U.S. Cl. ............................. 606/49; 606/41; 128/898
(58) Field of Classification Search .............. 606/41–50; 607/96, 98–102
   See application file for complete search history.

(56) References Cited

U.S. PATENT DOCUMENTS

| | | | |
|---|---|---|---|
| 1,229,704 A | 6/1917 | Berry | |
| 1,366,231 A | 1/1921 | Winter et al. | |
| 1,584,444 A | 4/1924 | Flick | |
| 2,030,285 A | 10/1934 | Dinyer | |
| 3,100,489 A | 8/1963 | Bagley | |
| 3,391,690 A | 7/1968 | Armao | |
| 3,613,682 A | 10/1971 | Naylor | |
| 3,662,151 A | 5/1972 | Haffey | |
| 3,978,312 A | 8/1976 | Barton et al. | |
| 3,980,861 A | 9/1976 | Fukunaga | |
| D253,303 S | 10/1979 | Barton et al. | |
| D254,150 S | 2/1980 | Barton et al. | |
| 4,274,413 A | 6/1981 | Hahn et al. | |
| 4,449,528 A | 5/1984 | Auth et al. | |
| 4,481,057 A | 11/1984 | Beard | |
| 4,485,810 A | 12/1984 | Beard | |
| 4,523,084 A | 6/1985 | Tamura et al. | |
| 4,549,073 A | 10/1985 | Tamura et al. | |
| 4,563,570 A | 1/1986 | Johns | |

(Continued)

OTHER PUBLICATIONS

Starion Instruments trade publication entitled "Cut and coagulate simultaneously with pure heat", 4 pages.

(Continued)

*Primary Examiner* — Aaron Roane
(74) *Attorney, Agent, or Firm* — Oblon, Spivak, McClelland, Maier & Neustadt, L.L.P.

(57) ABSTRACT

A portable, thermal cauterizing forceps device for use in surgery. The device incorporates a pair of ceramic heater elements mounted within the tips of the tines of a forceps. The forceps is used to grasp tissue or blood vessels and apply heat to effect cauterization. The forceps instrument can incorporate a battery and control electronics. The thermal-forceps is of a self-contained wireless, handheld disposable design. The forceps handpiece can be connected to an external power source. The forceps can incorporate a set of rapidly heating ceramic heater elements that may be composed of silicon nitride. An LED provides the operator feedback as to the operating level of the heaters and/or battery reserve. The forceps can include a rechargeable power supply, variable control of the heater temperature, as well as a, digital display of the tip temperature.

13 Claims, 7 Drawing Sheets

U.S. PATENT DOCUMENTS

| | | |
|---|---|---|
| 4,606,342 A | 8/1986 | Zamba et al. |
| 4,622,966 A | 11/1986 | Beard |
| 4,662,068 A | 5/1987 | Polonsky |
| 4,691,703 A | 9/1987 | Auth et al. |
| 4,708,136 A | 11/1987 | Saito |
| 4,744,359 A | 5/1988 | Hatta et al. |
| 4,787,373 A | 11/1988 | Vogel |
| 4,878,493 A | 11/1989 | Pasternak et al. |
| 5,026,370 A | 6/1991 | Lottick |
| 5,122,137 A | 6/1992 | Lennox |
| 5,250,046 A | 10/1993 | Lee |
| 5,306,287 A | 4/1994 | Becker |
| 5,352,868 A | 10/1994 | Denen et al. |
| 5,401,273 A | 3/1995 | Shippert |
| 5,443,463 A | 8/1995 | Stern et al. |
| 5,451,224 A | 9/1995 | Goble et al. |
| 5,452,513 A | 9/1995 | Zinnbauer et al. |
| 5,533,618 A | 7/1996 | Pickels, Jr. |
| 5,556,563 A | 9/1996 | Von Der Heyde et al. |
| 5,565,122 A | 10/1996 | Zinnbauer et al. |
| 5,688,265 A | 11/1997 | Citronowicz |
| 5,792,137 A | 8/1998 | Carr et al. |
| 5,792,138 A | 8/1998 | Shipp |
| 5,797,907 A | 8/1998 | Clement |
| 5,976,132 A | 11/1999 | Morris |
| 6,024,741 A | 2/2000 | Williamson, IV et al. |
| 6,039,729 A | 3/2000 | Durville et al. |
| 6,091,995 A | 7/2000 | Ingle et al. |
| 6,235,027 B1 | 5/2001 | Herzon |
| 6,277,117 B1 | 8/2001 | Tetzlaff et al. |
| 6,869,430 B2 | 3/2005 | Balbierz et al. |

OTHER PUBLICATIONS

Brochure entitled "The Hemostatix Thermal Scalpel", Smith + Nephew.

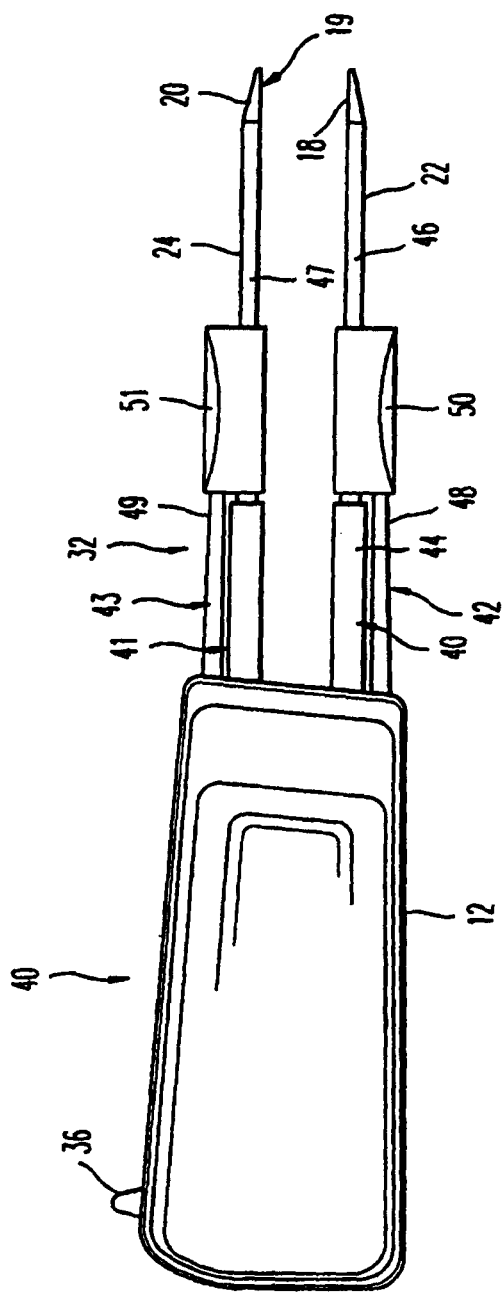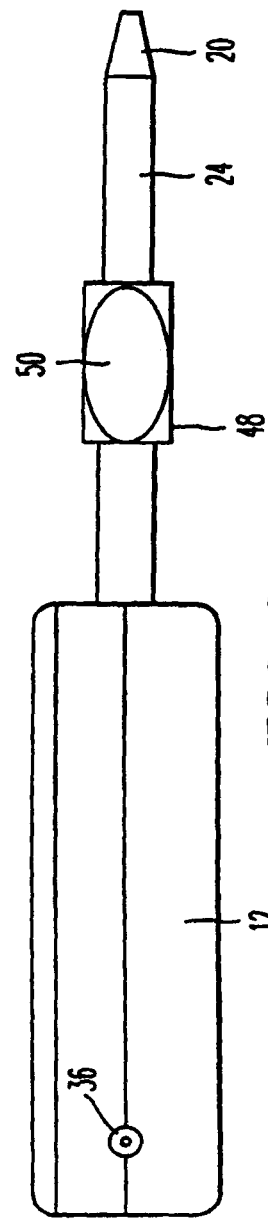
FIG. 1
FIG. 2

THERMAL CAUTERY SURGICAL FORCEPS

CROSS-REFERENCE TO RELATED APPLICATIONS

This application is a divisional of and claims the benefit of priority under 35 USC 120 from U.S. application Ser. No. 12/577,531 (now U.S. Pat. No. 8,128,623, issued Mar. 6, 2012), filed Oct. 12, 2009, which is a continuation of U.S. application Ser. No. 11/512,159 (now abandoned), filed Aug. 30, 2006, the entire contents of each of which are incorporated herein by reference. U.S. application Ser. No. 11/512,159, filed Aug. 30, 2006, is a continuation of U.S. Application Ser. No. 10/326,387 (now abandoned), filed Dec. 23, 2002, which is a continuation of U.S. application Ser. No. 09/842,140 (now U.S. Pat. No. 6,533,778, issued Mar. 18, 2003) filed Apr. 26, 2001, which is a continuation of U.S. application Ser. No. 09/235,229 (now U.S. Pat. No. 6,235,027, issued May 22, 2001) filed Jan. 21, 1999.

BACKGROUND OF THE INVENTION

The present invention relates to a handheld, portable thermal-cauterizing forceps including an integrated thermal heating surface disposed at each tip.

There are many surgical cautery devices available for the surgeon to ablate and vaporize tissue. Hot knives and cutting coagulators have been used to make skin incisions. The cautery can also be used in surgery to aid in hemostasis or control bleeding by coagulating blood vessels. Employing various cautery modalities decreases the duration of some surgical procedures by providing the surgeon a rapid method of coagulation without the need for suture ligation of blood vessels encountered during dissection.

Typically, surgical cautery is accomplished by directing a heating process onto tissue. The heat may be generated by either a thermal or electro-surgical process. Most commonly, an electro-surgical process using a radio frequency (RF) is used. The RF units generate heat by using high frequency electrical current and the resistive nature of tissue to produce heat. This technique requires a bulky generator and heavy electrical components to operate. Typically, RF electrocautery units require a power lead cable to the electro-surgical hand instrument and a large surface area grounding pad. More often than not, radio frequency surgical units are bulky expensive units which require a cable connection. Employing RF cauterization in a surgical operation may add significant cost to the procedure because the grounding pad, cable and handpiece must all be either re-sterilized or replaced in the case of disposable use.

A less common method of generating heat for coagulation of tissue is by thermal cautery. Thermal cautery is achieved by electrical heating of a resistive-wire loop or resistible electronic part by applying an electrical voltage. The prior art describes many handheld disposable, hot-wire loop cautery instruments. These devices have severe limitations as to their scope of use in surgery. The heat generated by the handheld battery powered devices is very small with a low heat capacity. The available patented devices are effective for cauterization of only the smallest of blood vessels, such as, vessels in the sclera of the eye. These battery powered hot-wire cautery instruments are not effective for use in cauterization of larger blood vessels encountered in most surgical procedures. A technique employing the electrical over driving of a zener diodes to produce heat has also been described in several patents. This device is primarily for limited endoscopic applications.

SUMMARY OF THE INVENTION

In order to overcome the limitations and disadvantages of the prior art, the present invention provides, in an embodiment, a new and improved hand-held, high energy, portable thermal cautery forceps. More particularly, the new and improved surgical forceps instrument includes an enclosure which houses a battery and electronic control. Active ceramic heaters are provided on the two tips of the operative end of the forceps. In a second embodiment, the thermal forceps may alternatively be powered by an external power source.

The new thermo-cautery forceps device in accordance with an embodiment of the invention provides the surgeon with several significant improvements in the state of the art. A first benefit of the thermal-cautery forceps is that it is cordless and fully portable. In the first embodiment of the invention, no cables or external power supply is necessary. This keeps the operative field clear of wires and cables. The thermal cautery of this invention does not require any grounding pad or foot switches.

A second benefit is the very high heating capacity of the thermal elements of the device. Temperatures of over 1000.degree. C. are easily obtainable. This heat capacity and temperature can easily cauterize medium and large blood vessels.

A third benefit provided by the new and improved thermal cautery forceps of the invention is its ability to heat to operating temperature in a very short time period, for example, within about one second. The preferred embodiment uses silicon nitride, ceramic heater elements. These new ceramic heaters exhibit rapid heating and cooling characteristics. Silicon nitride ceramic heaters have been used successfully in other fields outside surgery. To the inventor's knowledge, this is believed to be the first use within the field of surgical thermal coagulation.

In an alternative embodiment, less expensive alumina heaters and ceramic resistors or diodes may be employed in substitution for the silicon nitride ceramic heater elements to provide cost savings. However, such alternative types of heaters may be less preferred because longer times to obtain operating temperatures may be required.

A fourth advantage provided by the new and improved forceps is the placement of the thermal cautery heater elements at the ends of forceps tines. The unique position of the ceramic heater elements allows tissue and blood vessels to be easily grasped and directly coagulated in a controlled manner. The application of a closing or gripping pressure of the forceps against the tissue or vessel enhances the effectiveness of the coagulation.

A fifth benefit of the forceps device in accordance with the invention is to decrease the cost and enhance the availability of surgical cautery. The first embodiment of the thermal forceps allows for the device to be packaged as a sterile disposable instrument. The instrument can be used in emergency or field operations. The device may be used for hemostasis during outpatient surgical procedures in clinics and in surgery centers, as well as, at emergency scenes.

Other objects and advantages provided by the present invention will become apparent from the following Detailed Description taken in conjunction with the Drawings, in which:

BRIEF DESCRIPTION OF THE DRAWINGS

FIG. 1 is a side elevational view of the new and improved thermal cautery forceps instrument of the present invention in accordance with a first embodiment including an internal battery;

FIG. 2 is a top plan view of the new and improved thermal cautery forceps shown in FIG. 1;

DETAILED DESCRIPTION OF THE PREFERRED EMBODIMENT

Figure 3:
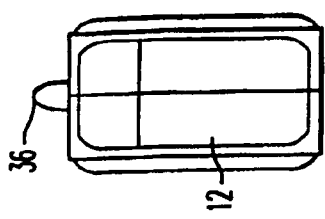
FIG. 3 is an end elevational view of the new and improved thermal cautery forceps showing the front or forceps tines end.

In accordance with a preferred embodiment of the invention, a new and improved thermocautery surgical forceps comprises a surgical forceps body including a pair of elongate tine members extending from the forceps body to respective free end tip portions spaced from the forceps body. The tine members are mounted to the forceps body in a manner providing resilient compressible movement of the tine members between a normally open position, wherein the tines are disposed in aligned, parallel, spaced-apart relationship, and a squeezed closed position, wherein the tip portions of the tine members are disposed in confronting abutting relationship. Each tine member includes a tissue contact surface defined on an inner facing surface of the tine member adjacent the tip portion. A ceramic heater element is disposed in each tine member so as to effectively heat the tissue contact surface to an elevated tissue cauterizing temperature. The ceramic heater elements are optionally connected to a power source. The tine members may be squeezed together to their squeezed closed position to grippingly, squeezably engage tissue to be cauterized between the tip portions. The tissue contact surfaces on the tines may be heated to a tissue cauterizing temperature to effectively thermocauterize the gripped tissue.

Referring now to FIGS. 1-6, a preferred embodiment of the new and improved thermocautery surgical forceps Generally designated by reference numeral 10 is shown. Forceps 10 includes a forceps body or housing 12 for the battery 14 and electrical control components 16. Specialized ceramic heating elements 18 are disposed on the tips 20 of the forceps tines 22, 24. FIGS. 1-6 relate to the first embodiment of the invention, that of a portable unit 10 with an internal battery supply 14. FIGS. 7-12 relate to the second embodiment of the invention, that of a cautery unit 26 configured as a thermal forceps 28 and an external power supply 30.

As shown in FIG. 1, the first embodiment of the cauterizing instrument 10 generally comprises a housing 12 and an integrated forceps tines assembly 32. The housing 12 encloses the battery 14, controller electronics 34, an LED 36 and an internal power switch 38. The forceps tines 22, 24 of the instrument, as shown in FIG. 1, exit from openings in the front end of the housing 12. The forceps assembly comprises two tines 22, 24 of equal length. Each tine 22, 24 is constructed of a heater-carrier 40 and an insulator cover-piece 42. The heater-carrier 40 comprises a metal arm 44 that supports an attached ceramic heater unit 46. The insulator cover-piece 42 is a shroud 48 that covers the heater 46 and its carrier arm 44. The shroud cover 48 is heat resistant and protects the surgeon's fingers from the heat generated by the ceramic heaters 46. The shroud 48 includes a recess 50 to fit the operators thumb and index finger to aid in holding the instrument. Inward compression on the shrouds 48 acts to compress the heater carrier arms 44 and will cause the switch 38 to close.

Figure 4:
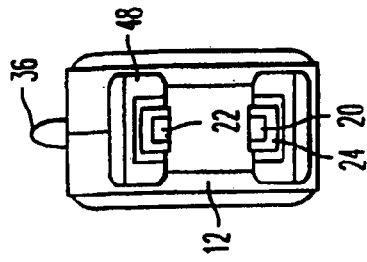
FIG. 4 is an end elevational view of the new and improved thermal cautery forceps viewed from the rear or opposite end of the forceps.

FIG. 2 shows a top view of the instruments with the LED exiting the rear of the housing enclosure and the forceps shroud cover with finger recess. The enclosure is rectangular in shape having a closed end and an open end. The open end allows the forceps assembly to exit from the enclosure. The enclosure is composed of a plastic formed with an injection process. The open end of the enclosure is shown in FIG. 3. The forceps are shown as well as the LED on the top of the housing. The position of the LED allows the surgeon easily visualize the operation of the instrument. The surgeon can see the LED while it is held in the hand and operated. FIG. 4 shows the closed end of the housing.

Figure 5:
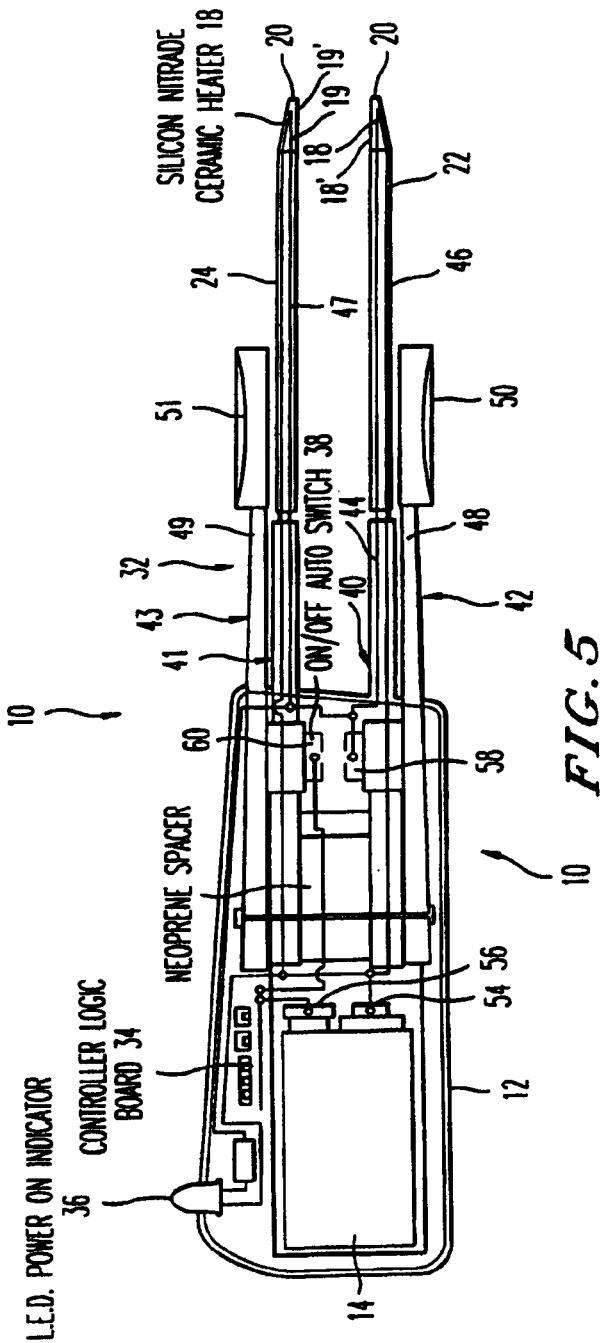
FIG. 5 is an elevated cross-sectional view of the new and improved thermal cautery forceps shown in FIGS. 1-4, showing the logic controller board, LED indicator lamp, internal switch and internal battery.

Shown in FIG. 5 is a cross-sectional view of the enclosure containing a battery for power supply. The battery may be rated form 3 volts to 24 VDC depending on the heating characteristics required. The battery may be of an alkaline or lithium cell. The battery positive and negative terminals are connected to the instrument circuitry by a terminal battery clip. Also, contained within the enclosure is a small circuit board that is populated with an integrated circuit and support components. The circuit board has connections to the power supply, LED, heater elements and switch mechanism. This circuit acts as a logic-controller to regulate the current delivered to the heating elements. The logic-controller circuit monitors the temperature and resistance of the heater elements and regulates the voltage supply. At the onset of operation the logic circuit allows high current to flow to the heaters aiding in initial rapid heating. The current is then reduced to maintain the heaters at a set temperature. The controller circuit logic also controls the LED to indicate the operative state of the heater elements. The LED will illuminate only if the battery power reserve or supply voltage attain a specified level and heaters reach the preset operational temperature. The logic controller also measures the internal resistance and temperature of the heater elements. The LED will fail to illuminate if these values fall outside the normal operational limits.

In an alternative design of the first embodiment a small piezoelectric speaker may be incorporated into the forceps enclosure. In the alternative design (not shown) the logic controller is further able to supply a piezo-electric speaker with supply voltage. The piezo-electric speaker provides the operator with auditory feedback pertaining to the operation of the instrument. The speaker emits a sound to give the surgeon an audio feedback as to the operation of the instrument. The sound indicates that the heating elements are at the normal operative temperature for effective cauterization.

Also shown in FIG. 5, is the mounting arrangement of the forceps tines. Each tine is mounted on opposite sides of a rectangular neoprene spacer. The pair of tines and neoprene spacer are fasted together by a binding pin with end caps. The off-center arrangement fastening of the tines to the neoprene spacer allows for a spring like tweezer effect.

An electrical open/close single pole switch is incorporated into the instrument. The switch is positioned within the housing enclosure between the base of the forceps tines. The switch is composed of two contacts that are brought into contact when the forceps are squeezed together. Closing the switch allows current to be delivered to the heaters. The contacts meet, as soon as, closure of the tines is begun and stays in a closed position as long as the tines are closed. Release of the forceps tines will open the switch and current supply to the heaters will terminate.

Figure 6:
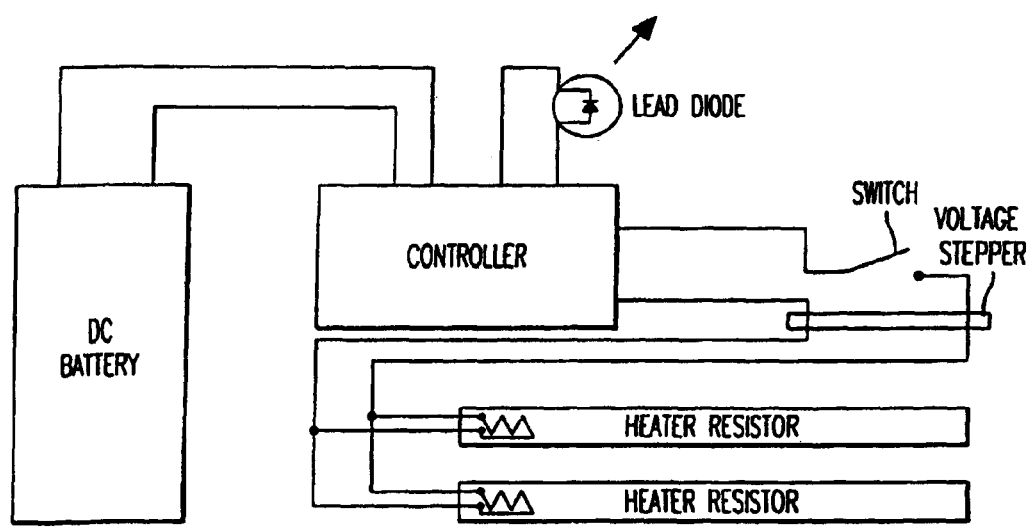
FIG. 6 is a schematic block diagram of the electrical circuit for the new and improved thermal cautery forceps of the first embodiment of the invention comprising a battery powered portable device.

The typical wiring diagram and schematic is shown in FIG. 6. The schematic shows a DC battery with positive and negative leads connected to a logic control circuit board. The circuit board is able to regulate the current delivered to the heater elements by measuring the internal electrical resistance of the heaters and the voltage available from the batteries. The controller also will vary the initial resistance of the heater circuit to obtain quick heat up at power on. The controller logic also controls the illumination of the LED. The LED is switched on when a preset temperature of the heaters is reached. The ON/OFF switch incorporated into the forceps is also depicted. The switch is closed upon closure of the forceps and allows a current to flow to the heaters. Two heaters are shown which are wired in parallel. The internal resistance of the heaters is about 5 to 10 ohms. The typical heater is composed of either alumina of silicon nitride or similar glass or ceramic material. This material specification is used due to high wattage density, rapid heat increase to 1000 degrees within one second, high level of insulation and non-stick nature of the ceramic to charred tissue.

Figures 7, 8:
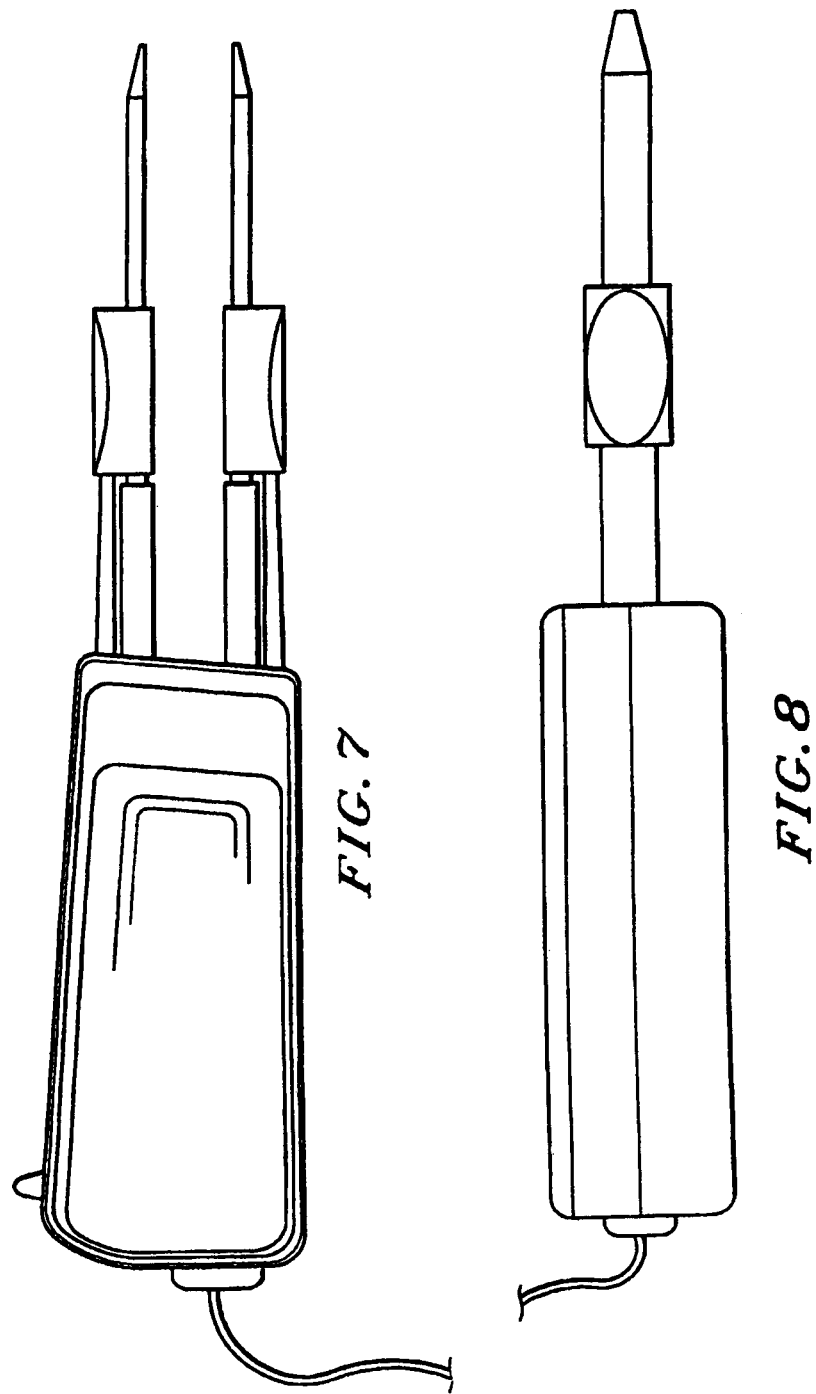
FIG. 7 is an elevated side view of the thermal cautery forceps instrument in accordance with a second embodiment of the invention including an external power supply unit.
FIG. 8 is a top plan view of the new and improved thermal cautery forceps shown in FIG. 7.
Figure 9:
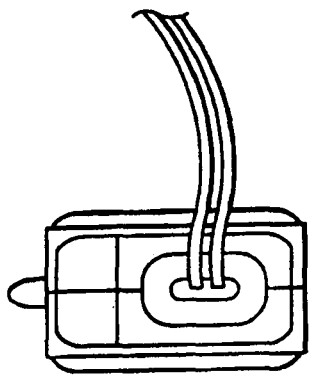
FIG. 9 is an elevated end view of the new and improved thermal cautery forceps of FIG. 7 taken from the forceps tine end.
Figure 10:
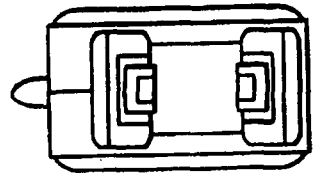
FIG. 10 is an elevated end view of the new and improved thermal cautery forceps shown in FIG. 7, taken from the opposite end and showing the cable connector.
Figure 11:
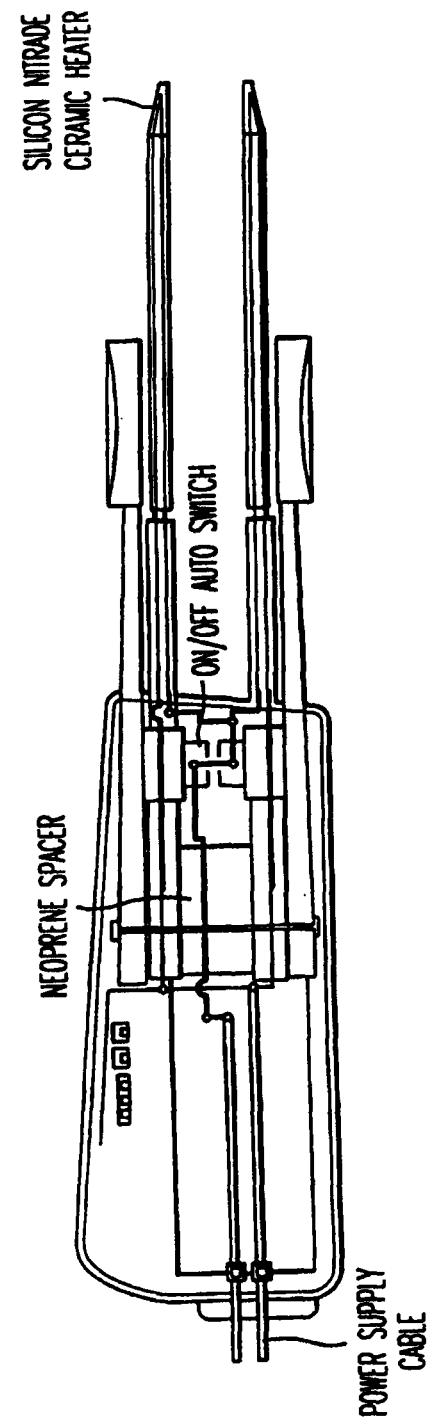
FIG. 11 is an elevated cross-sectional view of the new and improved thermal cautery forceps in accordance with the second embodiment, showing the housing and cable connection to the pair of heater units.

The second embodiment of the invention is shown in FIGS. 7-12. In this embodiment an external power source is used to power and control a simple thermal cautery forceps. The forceps in this embodiment is either of an inexpensive disposable or a more durable reusable design. FIGS. 7, 8, 10 and 11 show the externally powered cautery forceps. FIG. 7 is a side elevational view of the thermal cautery forceps instrument of the second embodiment of the invention. A cable connects the forceps to the external power supply unit is shown. As previously describe is the pair of forceps exiting from an enclosure. Each tine is composed of a rigid metal carrier with ceramic heater and an insulating plastic shroud. FIG. 8 is a top plan view thereof; FIG. 9 is an end elevational view there of illustrating the forceps tine end. FIG. 10 is an end elevational view of the end opposite the forceps illustrating the cable connector. FIG. 11 is a cross-sectional view of the second embodiment of the present invention, showing the housing and cable connection. A pair of wires connects the cable to a pair of thermal heater elements wire in parallel. Also shown in FIG. 11 is the neoprene spacer. The spacer is positioned between the forceps tines. An off center-binding pin through the tines and spacer provides a spring effect. The spring effect also activates the ON/OFF switch. The switch is composed of two electrical metal contacts affixed to the inside of each forceps tine.

Figure 12:
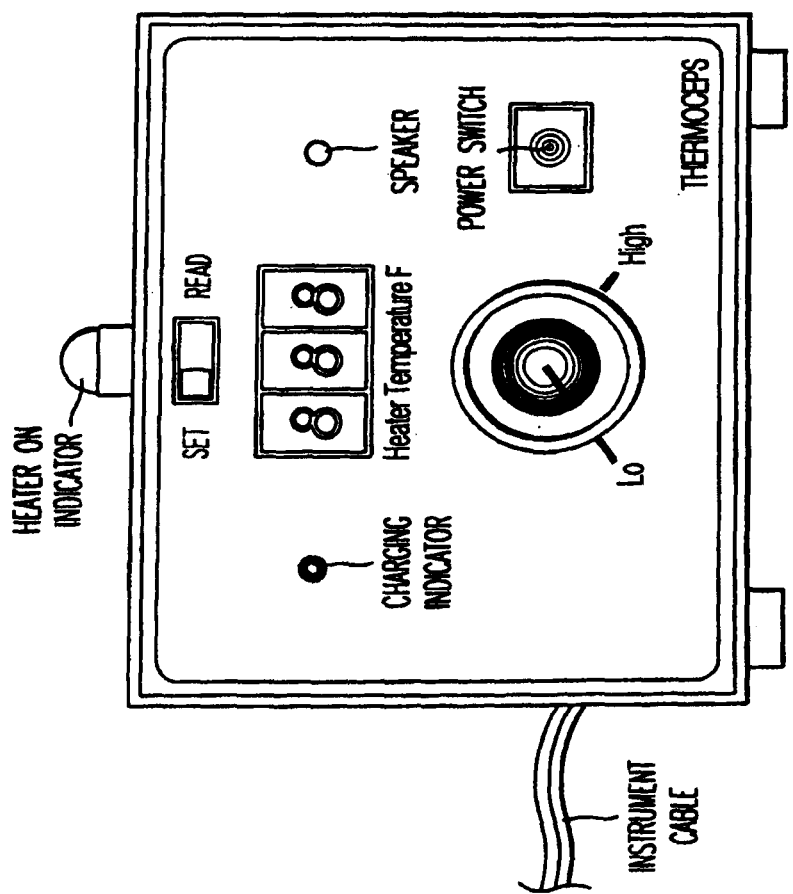
FIG. 12 is an elevated front view of the external power supply unit for use with the new and improved thermal cautery forceps in accordance with the second embodiment showing control features, including a power switch, audio speaker, temperature display, SET/READ switch, temperature control knob, recharging lamp and ready LED lamp.

FIG. 12 is a front elevation of the external power supply unit. This unit contains a power switch, audio speaker, digital temperature display, SET/READ switch, temperature control knob, recharging indicator lamp and ready LED lamp.

As shown in FIG. 12, a cable that connects to the forceps enters the power unit. A power switch is located on the front panel that illuminates when switch on. The external unit contains an audio amplifier with a small piezo-electric speaker. The speaker signals the surgeon of proper heater element temperature for cauterization. The speaker will sound when the instrument reaches the SET temperature after the forceps are squeezed together to initiate heating. The output of the speaker is vented outside the power unit through a small port shown in FIG. 12. The unit also contains a temperature control. The temperature may be varied by positioning the SET/READ switch to the SET position and rotating the temperature adjust knob to the desired temperature. The digital temperature display reports the desired set temperature in degrees fahrenheit. The temperature adjust control may either be of an analogue or digital type. This control allows the surgeon to select a temperature for a desired effect depending on the thickness and moisture content of the tissue to be cauterized. A digital temperature display may indicate the actual temperature of the ceramic heater elements when the SET/READ switch is positioned in the READ position. An LED indicator is incorporated into the power supply, which is illuminated when the batteries are recharging. This occurs whenever the power unit is connected to a 110 VAC line. A charging circuit regulates the recharging process.

Figure 13:
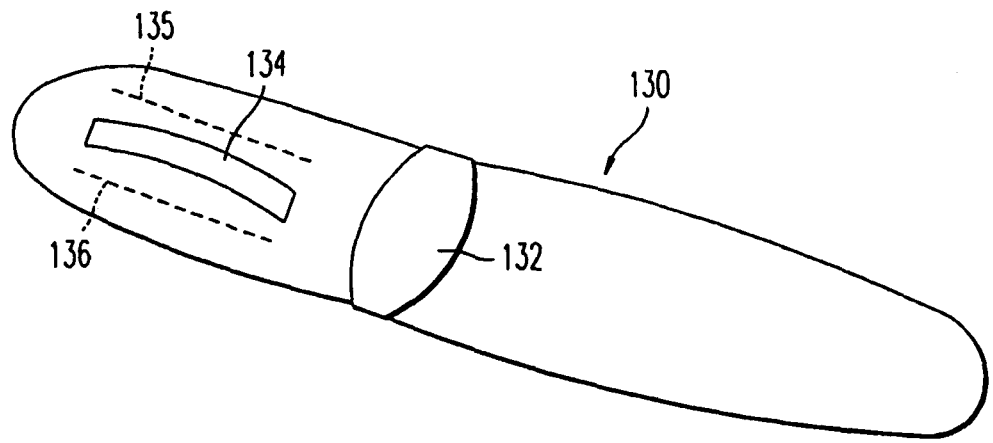
FIG. 13 is a perspective view of a holster for carrying a portable thermal cautery forceps made in accordance with one embodiment of the present invention.
Figure 14:
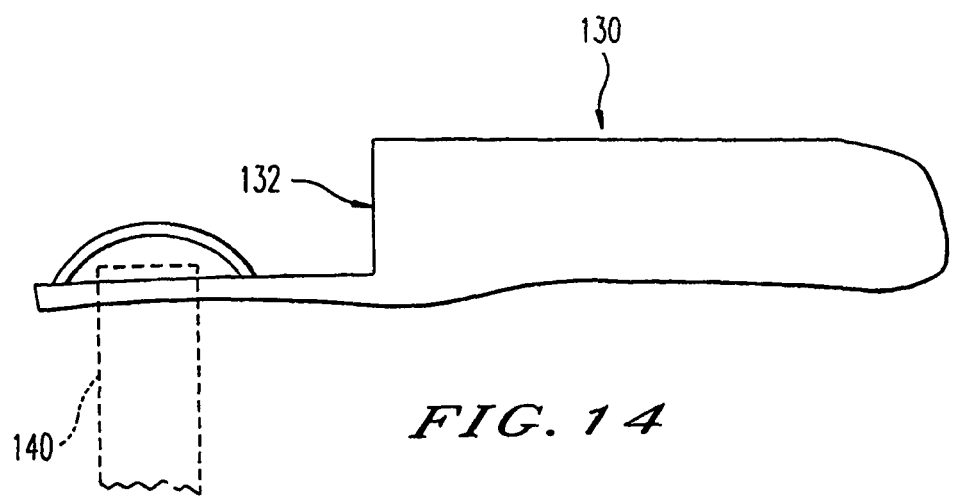
FIG. 14 is a side elevational view of the holster shown in FIG. 13.

FIGS. 13 and 14 illustrate a holster 130 for accommodating the forceps 10. A cavity 132 receives the tine end of the forceps 10. A loop 134 or slits 135, 136 may be provided for attaching the holster 130 to a belt 140.

The foregoing discussion of the invention has been presented for purposes of illustration and description. Further, the description is not intended to limit the invention to the form disclosed herein. Consequently, variations and modification commensurate with the above teachings, and the skill or knowledge in the relevant art, are within the scope of the present invention. The embodiments described herein above are further intended to explain modes known of practicing the invention and to enable others skilled in the art to utilize the invention in such, or other embodiments and with various modification required by their particular applications or uses of the invention. It is intended that the appended claim be construed to include alternative embodiments to the extent permitted by the prior art.

The invention claimed is:

1. A method for sealing and dividing blood vessels or thermocauterizing tissue with surgical forceps that include a forceps body and a pair of elongate tine members mounted to and extending from the forceps body to respective opposed free end tip portions spaced from the forceps body, the method comprising:

electrically connecting power source leads to a power supply, at least one of said tip portions of the tine members comprising a heater element connected to the power source leads and said heater element having a flat, gripping and heating surface defined on an inner facing surface of said at least one of said tip portions;

moving the tine members in a resilient compressible manner between a normally open position wherein the tine members are disposed in an aligned and spaced-apart relationship and a squeezed closed position wherein the tip portions of the tine members are disposed in a confronting abutting relationship;

activating the heater elements to heat the flat gripping and heating surfaces thereof to a tissue cauterizing or blood vessel sealing temperature;

supplying a high initial current to the heater element for rapid heat and then supplying a reduced current to said heater element for maintenance of the heat; and squeezing together the tine members toward the squeezed closed position to grippingly, squeezably, engage tissue to be cauterized or a blood vessel to be sealed between the flat gripping and heating surface of said heater element and the opposed tip portion.

2. The method of sealing and dividing blood vessels or thermocauterizing tissue according to claim 1, further comprising applying substantially uniform pressure and heat to a tissue gripped between the gripping and heating surfaces.

3. The method of sealing and dividing blood vessels or thermocauterizing tissue according to claim 1, further comprising:

indicating an operative state of said heater element;

measuring, with a circuit board, a battery power reserve or supply voltage and an internal resistance and a temperature of said heater element; and indicating whether the battery power reserve or supply voltage and the internal resistance and the temperature of said heater element falls within predetermined operational limits.

4. The method of sealing and dividing blood vessels or thermocauterizing tissue according to claim 1, further comprising electrically connecting a switch to the heater element and the power source leads and automatically turning on the heater element to heat the flat gripping and heating surface to an elevated tissue cauterizing or blood vessel sealing temperature as the tine members are moved from the normally open position to the squeezed closed position.

5. The method of sealing and dividing blood vessels or thermocauterizing tissue according to claim 1, further comprising connecting a rechargeable battery to said power source leads.

6. The method of sealing and dividing blood vessels or thermocauterizing tissue according to claim 1, further comprising connecting a battery to said power source leads.

7. The method of sealing and dividing blood vessels or thermocauterizing tissue according to claim 1, further comprising connecting an external power supply to said power source leads.

8. The method of sealing and dividing blood vessels or thermocauterizing tissue according to claim 1, further comprising receiving and holding the forceps body in a heat-resistant holster assembly.

9. The method of sealing and dividing blood vessels or thermocauterizing tissue according to claim 1, further comprising varying an initial resistance of a heater circuit to obtain heat rapidly.

10. The method of sealing and dividing blood vessels or thermocauterizing tissue according to claim 1, further comprising mounting each of said tine members of said pair of elongate tine members to opposite sides of a neoprene spacer for a spring effect.

11. The method of sealing and dividing blood vessels or thermocauterizing tissue according to claim 1, further comprising terminating the supply of current to the heater elements when the tip portions of the tine members are released from their confronting abutting relationship.

12. The method of sealing and dividing blood vessels or thermocauterizing tissue according to claim 1, further comprising emitting an audible sound from the forceps indicating an operational condition of the forceps.

13. The method of sealing and dividing blood vessels or thermocauterizing tissue according to claim 12, wherein the audible sound indicates whether the heating elements are at a normal operative temperature for effective cauterization.

* * * * *